US010034871B2

(12) United States Patent
Portoghese

(10) Patent No.: US 10,034,871 B2
(45) Date of Patent: Jul. 31, 2018

(54) SALTS AND COMPOSITIONS USEFUL FOR TREATING DISEASE

(71) Applicant: REGENTS OF THE UNIVERSITY OF MINNESOTA, Minneapolis, MN (US)

(72) Inventor: Philip Portoghese, Minneapolis, MN (US)

(73) Assignee: Regents of the University of Minnesota, Minneapolis, MN (US)

(*) Notice: Subject to any disclaimer, the term of this patent is extended or adjusted under 35 U.S.C. 154(b) by 0 days.

(21) Appl. No.: 15/524,116

(22) PCT Filed: Nov. 4, 2015

(86) PCT No.: PCT/US2015/059050
§ 371 (c)(1),
(2) Date: May 3, 2017

(87) PCT Pub. No.: WO2016/073615
PCT Pub. Date: May 12, 2016

(65) Prior Publication Data
US 2017/0333417 A1    Nov. 23, 2017

Related U.S. Application Data

(60) Provisional application No. 62/076,884, filed on Nov. 7, 2014.

(51) Int. Cl.
| | |
|---|---|
| *A61K 31/439* | (2006.01) |
| *C07D 471/18* | (2006.01) |
| *A61K 31/4525* | (2006.01) |
| *C07D 339/04* | (2006.01) |
| *C07D 489/08* | (2006.01) |
| *C07D 491/18* | (2006.01) |
| *A61K 31/454* | (2006.01) |
| *A61K 9/48* | (2006.01) |
| *A61K 31/7016* | (2006.01) |
| *A61K 45/06* | (2006.01) |

(52) U.S. Cl.
CPC ........ *A61K 31/4525* (2013.01); *A61K 31/454* (2013.01); *C07D 339/04* (2013.01); *C07D 489/08* (2013.01); *C07D 491/18* (2013.01); *A61K 9/4808* (2013.01); *A61K 31/7016* (2013.01); *A61K 45/06* (2013.01)

(58) Field of Classification Search
CPC ............................ A61K 31/439; C07D 471/18
USPC ............................................. 514/279; 546/35
See application file for complete search history.

(56) References Cited

U.S. PATENT DOCUMENTS

| | | | |
|---|---|---|---|
| 4,272,540 A | 6/1981 | Razdan et al. | |
| 4,451,470 A | 5/1984 | Ganti | |
| 4,478,840 A | 10/1984 | Smith, Jr. | |
| 4,619,936 A | 10/1986 | Balkanyi et al. | |
| 4,649,200 A | 3/1987 | Portoghese et al. | |
| 4,816,586 A | 3/1989 | Portoghese | |
| 4,882,335 A | 11/1989 | Sinclair | |
| 5,086,058 A | 2/1992 | Sinclair et al. | |
| 5,208,250 A | 5/1993 | Cetenko et al. | |
| 5,428,066 A | 6/1995 | Larner et al. | |
| 5,457,208 A | 10/1995 | Portoghese et al. | |
| 5,578,725 A | 11/1996 | Portoghese et al. | |
| 5,665,383 A | 9/1997 | Grinstaff et al. | |
| 5,727,570 A | 3/1998 | Clemens | |
| 5,772,629 A | 6/1998 | Kaplan | |
| 5,866,595 A | 2/1999 | Pershadsingh et al. | |
| 5,878,750 A | 3/1999 | Clemens | |
| 5,886,001 A | 3/1999 | Schmidhammer | |
| 5,891,909 A | 4/1999 | Soll et al. | |
| 5,925,657 A | 7/1999 | Seed et al. | |
| 6,026,817 A | 2/2000 | Clemens | |
| 6,087,385 A | 7/2000 | Pershadsingh et al. | |
| 6,242,196 B1 | 6/2001 | Spiegelman et al. | |
| 6,258,121 B1 | 7/2001 | Yang et al. | |
| 6,262,062 B1 | 7/2001 | Clemens | |
| 6,268,357 B1 | 7/2001 | Orvig et al. | |
| 6,280,411 B1 | 8/2001 | Lennox | |
| 6,294,559 B1 | 9/2001 | Smith | |
| 6,309,660 B1 | 10/2001 | Hsu et al. | |
| 6,364,893 B1 | 4/2002 | Sahatjian et al. | |
| 6,369,039 B1 | 4/2002 | Palasis et al. | |
| 6,387,121 B1 | 5/2002 | Alt | |
| 6,409,716 B1 | 6/2002 | Sahatjian et al. | |
| 6,410,802 B1 | 6/2002 | Dasseux et al. | |
| 6,417,232 B1 | 7/2002 | Berge | |
| 6,419,692 B1 | 7/2002 | Yang et al. | |
| 6,441,025 B2 | 8/2002 | Li et al. | |
| 6,458,952 B1 | 10/2002 | South et al. | |
| 6,459,003 B1 | 10/2002 | Dasseux et al. | |

(Continued)

FOREIGN PATENT DOCUMENTS

| | | |
|---|---|---|
| BE | 876382 A | 11/1979 |
| EP | 0078434 A1 | 5/1983 |

(Continued)

OTHER PUBLICATIONS

Jacob, "Studies on the role of tumor necrosis factor in murine and human autoimmunity", J Autoimmun 5 (Suppl A), 133-143 (1992).
Jacob, et al., "Thioctic acid—effects on insulin sensitivity and glucose-metabolism", Biofactors 10(2-3), 169-174 (1999).
Jarosz, et al., "Effect of chronic kappa opioid receptor antagonism on body weight and food intake in obese Zucker rats", Neuroscience 2000 Abstract, 1 page. (2000).
Jewett, et al., "The kappa-opioid antagonist GNTI reduces U50,488-, DAMGO-, and deprivation-induced feeding, but not butorphanol- and neuropeptide Y-induced feeding in rats", Brain Research 909, 75-80 (2001).
Jivegard, et al., "The influence of morphine, loperamide and naloxone on gallbladder response to prostaglandin E2 in the anaesthetized cat", Acta Physiol Scand 127, 275-279 (1986).
Jones, et al., "Mutational Evidence for a Common k Antagonist Binding Pocket in the Wild-Type k and Mutant μ [K308E] Opioid Receptors", Journal of Med Chem 41(25), 4911-4914 (1998).

(Continued)

*Primary Examiner* — Brenda L Coleman
(74) *Attorney, Agent, or Firm* — Viksnins Harris Padys Malen LLP

(57) ABSTRACT

The invention provides a combination or salt of lipoic acid and a compound of formula (I): The combinations and salts are useful for treating diabetes.

5 Claims, 2 Drawing Sheets

(56) References Cited

U.S. PATENT DOCUMENTS

| | | |
|---|---|---|
| 6,471,979 B2 | 10/2002 | New et al. |
| 6,475,521 B1 | 11/2002 | Timmins et al. |
| 6,500,824 B1 | 12/2002 | Portoghese et al. |
| 6,528,520 B2 | 3/2003 | Clemens |
| 6,534,514 B1 | 3/2003 | Portoghese et al. |
| 6,846,831 B2 | 1/2005 | Clemens |
| 6,910,310 B2 | 6/2005 | Bower et al. |
| 7,893,080 B2 | 2/2011 | Clemens |
| 8,445,508 B2 | 5/2013 | Clemens |
| 8,829,018 B2 | 9/2014 | Clemens |
| 2005/0250701 A1 | 11/2005 | Clemens |
| 2008/0108640 A1 | 5/2008 | Clemens |
| 2012/0101107 A1 | 4/2012 | Kim et al. |

FOREIGN PATENT DOCUMENTS

| | | |
|---|---|---|
| EP | 0541192 A1 | 5/1993 |
| GB | 2045758 A | 11/1980 |
| WO | 1993000337 A1 | 1/1993 |
| WO | 1997018781 A1 | 5/1997 |
| WO | 1997035608 A1 | 10/1997 |
| WO | 1999004795 A1 | 2/1999 |
| WO | 1999059997 A1 | 11/1999 |
| WO | 2002013759 A2 | 2/2002 |
| WO | 2002013801 A2 | 2/2002 |
| WO | 2002100390 A2 | 12/2002 |
| WO | 2003026635 A2 | 4/2003 |
| WO | 2008051902 A2 | 5/2008 |
| WO | 2010056726 A1 | 5/2010 |

OTHER PUBLICATIONS

Khawaja, et al., "Increased Sensitivity to Insulin-Releasing and glucoregulatory Effects of Dynorphin A1-13 and U 50488h in ob/ob Versus Lean Mice", Diabetes 39, 1289-1297 (1990).

Kindmark, et al., "Glucose-Dependent Insulinotropic Hormone Potentiates the Hypoglycemic Effect of Glibenclamide in Healthy Volunteers: Evidence for an Effect on Insulin Extraction", Journal of Clinical Endocrinology & Metabolism 86(5), 2015-2019 (2001).

Kurtz, et al., "Nalmefene, an orally active opiate antagonist, reduces Insulin Resistane and Caloric Intake in Obese Women with Polycystic Overies and Acanthoisis Nigricans", Abstract, 1 page (1985).

Landgraf, et al., "Prolactin: A Diabetogenic Hormone", Diabetologia 13, 99-104 (1977).

Leslie, et al., "Sensitivity to Enkephalin as a Cause of Non-Insulin Dependent Diabetes", The Lancet 341-343 (Feb. 17, 1979).

Levine, et al., "Effect of chronic administration of morphine and nalmefene on food intake and body weight in diabetic and control rats", 55 Abstract, 1 page (1985).

Levine, et al., "Nor-binaltorphimine decreases deprivation and opioid-induced feeding", Brain Research 534(1-2), 60-64, 1 page Abstract (1990).

Lewis, "Buprenorphine", Drug and Alcohol Dependence 14, 363-372 (1985).

Lewis, et al., "Glucose-Dependent Insulinotropic Polypeptide Confers Early Phase Insulin Release to Oral Glucose in Rats: Demonstration by a Receptor Antagonist", Endocrinology 141(10), 3710-3716 (2000).

Liang, et al., "Direct Preconditioning of Cardiac Myocytes via Opioid Receptors and KATP Channels", Circ Res 8, 1396-1400 (1999).

Linner, et al., "The δ1-opioid receptor antagonist, 7-benzylspiroindanylnaltrexone, prolongs renal allograft survival in a rat model", European Journal of Pharmacology 354, R3-R5 (1998).

Liu, et al., "Activation of opioid μ-receptor by loperamide to lower plasma glucose in streptozotocin-induced diabetic rats", Neuroscience Letters 265, 183-186 (1999).

Malaisse, et al., "Insulinotropic action of beta-L-glucose pentaacetate", Endocrinol Metab 38, E993-E1006 (1998).

Marsboom, et al., "Loperamide (R 18553), a Novel Type of Antidiarrheal Agent", Drug Res 24(10), 1645-1649.

Martinez, et al., "Metabolic abnormalities and body fat redistribution in HIV-1 infected patients: the lipodystrophy syndrome", Curr Opin Infect Dis 12, 13-19 (1999).

McCormack, et al., "Opioid Receptors and Myocardial Protection Do Opioid Agonists Possess Cardioprotective Effects?", Clin Drug Invest 15(5), 445-454 (1998).

McCubbin, et al., "Opioidergic Inhibition of Circulatory and Endocrine Stress Responses in Cynomolgus Monkeys: A Preliminary Study", Psychosomatic Medicine 55, 23-28 (1993).

McIntosh, et al., "Effects of selective opioid receptor agonists and antagonists during myocardial ischaemia", European Journal of Pharmacology 210, 37-44 (1992).

McIntosh, et al., "The Effects of Opioid Receptor Selective Antagonists and Agonists Following Coronary Artery Occlusion in Anesthetized Rats", PF51 Abstract, S.72, 1 page. (1990).

McLaughlin, et al., "Glucose, insulin, food intake and body weight response of Zuker rates to nalmefene, an opiate antagonist", Abstract 965, S372, 1 page (1985).

McLaughlin, et al., "Influence of Nalmefene on Energy Balance and Glucose Regulation in Zucker Rats", Physiology & Behavior 37, 899-908 (1986).

McLaughlin, et al., "Nalmefene Decreases Meal Size, Food and Water Intake and Weight Gain in Zucker Rats", Pharmacology Biochemistry & Behavior 19, 235-240 (1983).

McQuay, et al., "Clinical Effects of Buprenorphine During and After Operation", Br J Anaesth 52, 1013-1019 (1980).

Meier, et al., "Postprandial Suppression of Glucagon Secretion Depends on Intact Pulsatile Insulin Secretion. Further Evidence for the Intraislet Insulin Hypothesis", Diabetes 55, 1051-1056 (2006).

Merz, "Structural features of opioid k agonists and antagonists", Adv Biochem Psychopharm 8, 91-107 (1974).

Metcalf, et al., "Kappa Opioid Antagonists: Past Successes and Future Prospects", The AAPS Journal 7(3), E704-E722 (2005).

Nauck, et al., "Gastric Inhibitory Polypeptide and Glucagon-Like Peptide-1 in the Pathogenesis of Type 2 Diabetes", Diabetes 53(Supp 3), S190-S196 (2004).

Niwa, et al., "Acetylcholine Activates Intracellular Movement of Insulin Granules in Pancreatic beta-Cells Via Inositol Triphosphate-Dependent Mobilization of Intracellular Ca2", Diabetes 47, 1699-1706 (1998).

Ofei, et al., "Effects of an Engineered Human Anti-TNF-α Antibody (CDP571) on Insulin Sensitivity and Glycemic Control in Patients with NIDDM", Diabetes 45, 881-885 (1996).

Pan, "μ-Opposing actions of the k-opioid receptor", TiPS 19, 94-98 (1998).

Paquot, "No Increased Insulin Sensitivity after a Single Intravenous Administration of a Recombinant Human Tumor Necrosis Factor Receptor: Fc Fusion Protein in Obese Insulin-Resistant Patients", Journal of Clinical Endocrinology & Metabolism 85(3), 1316-1319 (2000).

Parkes, et al., "Insulinotropic Actions of Exendin-4 and Glucagon-Like Peptide-1 In Vivo and In Vitro", Metabolism 50(5), 583-589 (2001).

Patent Cooperation Treaty, International Searching Authority, Search Report and Written Opinion for PCT/US2015/059050, 9 pages, dated Mar. 2, 2016.

Pearce, et al., "Effects of x-opioid and AVP-V1 receptor antagonists on the compensatory hemodynamic responses of anesthetized rates following acute hemorrhage", Can J Physiol Pharmacol 70, Abstract, 2 pages (1992).

Pfeifer, et al., "Insulin Secretion in Diabetes Mellitus", The American Journal of Medicine 70, 579-588 (1981).

Pfeiffer, et al., "Circulating Tumor Necrosis Factor α is Elevated in Male but Not in Female Patients with Type II Diabetes Mellitus", Horm Metab Res 29, 111-114 (1997).

Portoghese, et al., "Binaltorphimine and Nor-Binaltorphimine, Potent and Selective Opioid Receptor Antagonists", Life Sciences 40, 1287-1292 (1987).

Portoghese, et al., "Editorial—Expansion of the Perspective Series", J Med Chem 36(1), 179-180 (1993).

(56) References Cited

OTHER PUBLICATIONS

Portoghese, et al., "Tena, A Selective Kappa Opioid Receptor Antagonist", Life Sciences 36, 801-805 (1984).
Raskin, et al., "Repaglinide/Troglitazone Combination Therapy. Improved glycemic control in type 2 diabetes", Diabetes Care 23(7), 979-983 (2000).
Riepl, et al., "Pancreatic Polypeptide Release Induced by Ceruletide, Sham Feeding, and Hypoglycemia is Suppressed by Loperamide", Metab, 46, Abstract, 1 page (1983).
Riepl, et al., "Suppression of vagus-mediated pancreatic polypeptide release by the µ-opiate receptor agonist operamide in man", Br J Clin Pharmacol 42, 371-377 (1996).
Ruppin, "Review: loperamide—a potent antidiarrhoeal drug with actions along with the alimentary tract", Aliment Pharmacol Ther 1(3), 179-190 (1987).
Schultz, et al., "Morphine Mimics the Cardioprotective Effect of Ischemic Preconditioning via a Glibenclamide-Sensitive Mechanism in the Rat Heart", Circulation Research 78(6), 1100-1104 (1996).
Ahlgren, "Insulin-like action of morphine and certain morphine derivatives", Skandinavisches Archiv fuer Physiologie 58, 153-172, 1 page Abstract (1930).
Ahren, "Effects of Beta-Endorphin, met-Enkephalin, and Dynorphin A on Basal and Stimulated Insulin Secretion in the Mouse", International Journal of Pancreatology 5, 165-178 (1989).
Arias, et al., "Influence of Selective Agonist K Peripheral ICI-204448 (ICI) on Blood Pressure of Rats Pretreated with Clonidine (CLO)", 92 Oral Communications, O-34 Abstract, 1 page (1997).
Arioglu, et al., "Efficacy and Safety of Troglitazone in the Treatment of Lipodystrophy Syndromes", Ann Intern Med 133, 263-274 (2000).
Atkinson, et al., "Effects of long-term therapy with naltrexone on body weight in obesity", Clin Pharmacol Ther 38(4), 419-422 (1985).
Awoke, et al., "Alterations of Plasma Opioid Activity in Human Diabetics", Life Sciences 34(21), 1999-2006 (1984).
Bailey, et al., "Increased responsiveness to glucoregulatory effect of opiates in obese-diabetic ob/ob mice", Diabetologia 30(1), 33-37, 1 page Abstract (1987).
Bernardi, et al., "Endogenous Opioid System in Acute Myocardial Infarction", 141 Abstract, 1 page (1984).
Bertalmio, et al., "Differentiation between mu and kappa receptor-mediated effects in opioid drug discrimination: apparent pA2 analysis", Journal Pharmacology and Experimental Therapeutics 243(2), 591-597 (1987).
Buzi, et al., "Loperamide test: a simple and highly specific screening test for hypercortisolism in children and adolescents", Acta Paediatr 86, 1177-1180 (1997).
Caldara, et al., "Effect of Loperamide, a Peripheral Opiate Agonist, on Circulating Glucose, Free Fatty Acids, Insulin, C-Peptide and Pituitary Hormones in Healthy Man", Eur J Clin Pharmacol 21, 185-188 (1981).
Caldwell, et al., "Actions of the Opioid Antagonist, Nalmefene, and Congeners on Reperfusion Cardiac Arrhythmias and Regional Left Coronary Blood Flow", Pharmacology 41, 161-166 (1990).
Carr, et al., "The Roe of Opioids in Feeding and Reward Elicited by Lateral Hypothalamic Electrical Stimulation", Life Sciences 33(Supp I), 563-566 (1983).
Carroll, et al., "Pharmacological progperties of JDTic: a novel k-opioid receptor antagonist", European Journal of Pharmacology 501, 111-119 (2004).
Chance, et al., "Analysis of the Interaction of Naltrexone with Eating Following Adrenergic and Cholinergic Stimulation of the Hypothalamus", Neuropharmacology 21, 929-932 (1982).
Cole, et al., "Evaluation of Chronic Opioid Receptor Antagonist Effects Upon Weight and Intake Measures in Lean and Obese Zucker Rats", Peptides 18(8), 1201-1207 (1997).
Drolet, et al., "Endogenous opioids tonically inhibit the depressor neurones in the caudal ventrolateral medulla of rabbits: Mediation through δ- and κ-receptors", Neuropharmacology 30(4), 383-390 (1991).
Drucker, "Enhancing Incretin Action for the Treatment of Type 2 Diabetes", Diabetes Care 26, 2929-2940 (2003).
Edelman, "Prescribing Oral Antidiabetic Agents: General Considerations", Clinical Diabetes 16(1), 37-40 (1998).
European Search Report, for EP Application No. 07844505.3, 10 pages, dated Mar. 15, 2010.
Evans, et al., "Recent Developments and Emerging Therapies for Type 2 Diabetes Mellitus", Drugs 2(2), 75-94 (1999).
Felber, et al., "Effect of a 3-Day Fast on Glucose Storage and Oxidation in Obese Hyperinsulinemic Diabetics", Metabolism 30(2), 184-189 (1981).
Felber, et al., "Glucose Storage and Oxidation in Different Degrees of Human Obesity Measured by Continuous Indirect Calorimetry", Diabetologia 20, 39-4 (1981).
Ferlito, "Influenza dei peptidi oppioidi sul metabolismo glucidico", Progr. Med., Roma 41, 639-655 (1985). [English Summary].
Foss, et al., "Restoration of Glucose Homeostasis in Insulin-dependent Diabetic Subjects, An Inducible Process", Diabetes 31, 46-53 (1982).
Garris, "Nalmefene, an opiate antagonist, effectively modulates insulin receptor binding in the peripheral tissues of C57BL/KsJ mice", Med Sci Res 16, 301-302 (1988).
Gautret, et al., "Vagally Mediated Reflex and Cardiac Slowing Induced by Loperamide in Rats", European Journal of Pharmacology 107, 157-160 (1985).
Giugliano, et al., "beta-Endorphin and islet hormone release in type-2 diabetes mellitus. The effects of normoglycemia, enkephalin, naloxone and somatostatin", Diabete et Metabolisme 13(6), 618-624, 1 page Abstract (1987).
Giugliano, et al., "Impaired insulin secretion in human diabetes mellitus. The effect of naloxone-induced opiate receptor blockade", Diabetes 31(4), 367-370, 1 page Abstract (1982).
Giugliano, et al., "Sensitivity to Beta-Endorphin as a Cause of Human Obesity", Metabolism 36(10), 974-978 (1987).
Givens, et al., "Reduction of Hyperinsulinemia and Insulin Resistance by Opiate Receptor Blockade in the Polycystic Ovary Syndrome with Acanthosis Nigricans", Journal of Clinical Endocrinology and Metabolism 64(2), 377-382 (1987).
Goodman and Gilman's, "The Pharmacological Basis of Therapeutics", Seventh Edition, Chapt 18, The Aliphatic Alcohols, 382-383 (1985).
Got, et al., "Les Particularites Du Traitement Medical Chez Les Arteritiques Diabetiques", Journal des Maladies Vasculaires (Paris) 18, 30-36 (1993). [English Abstract].
Green, et al., "Effect of enkephalins and morphine on insulin secretion from isolated rat islets", Diabetologia 19(2), 158-191, 1 page Abstract (1980).
Green, et al., "Opiate-Prostaglandin Interactions in the Regulation of Insulin Secretion From Rat Islets of Langerhans In Vitro", Life Sciences 42, 2123-2130 (1988).
Green, et al., "Opioid peptide effects on isolated hepatocytes and islets of Langerhans", AN 105:203461, International Congress Series (1986), 700 (Diabetes 1985), 258-262 CODEN: EXMDA4; ISSN: 0531-5131, 1 page Abstract.
Greenbaum, et al., "Impaired beta-Cell Function, Incretin Effect, and Glucagon Suppression in Patients with Type 1 Diabetes Who Have Normal Fasting Glucose", Diabetes 51, 951-957 (2002).
Grundy, et al., "Definition of Metabolic Syndrome. Report of the National Heart, Lung, and Blood Institute/American Heart Association Conference on Scientific Issues Related to Definition", Circulation 109, 433-438 (2004).
Grundy, et al., "Diagnosis and Management of the Metabolic Syndrome. An American Heart Association/National Heart, Lung, and Blood Institute Scientific Statement", Circulation 112, 2735-2752 (2005).
Grundy, et al., "Diagnosis and Management of the Metabolic Syndrome. An American Heart Association/National Heart, Lung, and Blood Institute Scientific Statement", Circulation 112, e285-e290 (2005).

(56) References Cited

OTHER PUBLICATIONS

Gupta, et al., "Glucose Homeostasis and Drugs Acting on CNS: Interactions with Antidiabetic Agents", Indian Journal of Pharmacology 26, 169-178 (1994).
Herz, "Bidirectional Effects of Opioids in Motivational Processes and the Involvement of D1 Dopamine Receptors", Problems of Drug Dependence 1988, Proceedings of the 50th Annual Scientific Meeting, Abstract, 12 pages (NIDA Res Monogr 90, 17-26) (1988).
Herz, "Opioid reward mechanisms: a key role in drug abuse?", Can J Physiol Pharmacol 76, 252-258 (1998).
Hiriart, et al., "Muscarinic modulation of insulin secretion by single pancreatic beta-cells", Molecular and Cellular Endocrinology 93, 63-69 (1993).
Holst, et al., "The Incretin Approach for Diabetes Treatment. Modulation of Islet Hormone Release by GLP-1 Agonism", Diabetes 53 (Suppl. 3), S197-S204 (2004).
Hotamisligil, et al., "Adipose Expression of Tumor Necrosis Factor-α: Direct Role in Obesity-Linked Insulin Resistance", Science 259, 87-91 (1993).
Hotamisligil, et al., "Tumor necrosis factor α inhibits signaling from the insulin receptor", Proc Natl Acad Sci 91, 4854-4854 (1994).
Imai, et al., "Effects of Opioid Antagonism in congestive heart failure", 992 Abstract, 1 page (1985).
Jacob, et al., "Enhancement of glucose disposal in patients with type 2 diabetes by alpha-lipoic acid", Arzneimittel-Forschung/Drug Research, 45(8), 872-874 (1995).
Jacob, et al., "Improvement of insulin-stimulated glucose-disposal in type 2 diabetes after repeated parenteral administration of thioctic acid", Exp Clin Endocrinol Diabetes 104(3), 284-288 (1996).
Shaw, et al., "The effect of the opioid antagonist LY255582 on body weight of the obese Zucker rat", International Journal of Obesity 15, 387-395 (1991).
Simpkins, et al., "Effects of Narcotic Antagonist, Naimefene, on Spontaneous and Insulin-Induced Food Intake and body Weight Gain in Male Rats", 21.7, Abstract, 1 page (1985).
Sohel, et al., "Influence of Adrenergic Blockers and Antilipemic Agents on Pharmacodynamic Actions of Morphine in Carbon Tetrachloride-Treated Rats", Toxicology and Applied Pharmacology 27, 477-483 (1974).
Spanagel, et al., "Evidence that nor-binaltorphimine can function as an antagonist at multiple opioid receptor subtypes", European Journal of Pharmacology 264, 157-162 (1994).
Stephens, et al., "Tumor necrosis factor-alpha-activated cell death pathways in NIT-1 insulinoma cells and primary pancreatic beta cells", Endocrinology 140(7), 3219-3227, 1 page Abstract (1999).
Stern, et al., "Lack of Awareness and Treatment of Hyperlipidemia in Type II Diabetes in a Community Survey", JAMA 262(3), 360-364 (1989).
Stevens, et al., "Potent and Selective Indolomorphinan Antagonists of the Kappa-Opioid Receptor", J Med Chem 43, 2759-2769 (2000).
Swidan, et al., "Effect of blood glucose concentrations on the development of chronic complications of diabetes mellitus", Pharmacotherapy 18(5), 961-972, 1 page Abstract (1998).
Szilagyi, "Phychosocial Stress Elevates Blood Pressure via an Opioid Dependent Mechanism in Normotensive Rats", Clin and Exper Hyper Theory and Practice A13(8), 1383-1394 (1991).
Szkudelski, et al., "The Effect of Myo-Inositol on Ethanol-Induced Metabolic Changes and Insulin Concentration in the Rat", Archives of Physiology and Biochemistry 107(4), 334-337 (1999).
Table, "Characteristics of Sulfonylurea and Antihyperglycemic Drugs", Chapter 13—Disorders of Carbohydrate Metabolism, p. 175 (1999).
Van Loon, et al., "Beta-Endorphin-Induced Stimulation of Central Sympathetic Outflow: Beta-Endorphin Increases Plasma Concentrations of Epinephrine, Norepinephrine, and Dopamine in Rats", Endocrinology 109(1), 46-53 (1981).
Verspohl, et al., "The significance of mu- and delta-receptors in rat pancreatic islets for the opioid-mediated insulin release", Biochimica et biophysica acta (Netherlands), 888(2), 217-224, 1 page Abstract (1986).
Vink, et al., "k-Opioid antagonist improves cellular bioenergetics and recovery after traumatic brain injury", American Physiological Society, R1527-R1532 (1991).
Wexler, et al., "Anti-opiate (Naloxone) Suppression of Cushingoid Degenerative Changes in Obese/SHR", International Journal of Obesity 9, 77-91 (1985).
Wexler, "Naloxone Ameliorates the Pathophysiologic Changes Which Lead to and Attend an Acute Stroke in Stroke-Prone/SHR", Stroke 15(4), 630-634 (1984).
Windholz, et al., "The Merck Index an Encyclopedia of Chemicals, Drugs and Biologicals", Tenth Edition, 491-492 (1983).
Yim, et al., "Opioids, feeding and anorexias", Federation Proceedings 43(14), 2893-2897, 1 page Abstract (1984).
Ziegler, "Thioctic Acid for Patients with Symptomatic Diabetic Polyneuropathy", Treat Endocrinol 3(3), 173-189 (2004).

SALTS AND COMPOSITIONS USEFUL FOR TREATING DISEASE

RELATED APPLICATION

This application claims priority to U.S. Provisional Application No. 62/076,884, filed 7 Nov. 2014, the entire content of which is incorporated herein by reference.

BACKGROUND

Endogenous opioid peptides are involved in the mediation or modulation of a variety of mammalian physiological processes, many of which are mimicked by opiates or other non-endogenous opioid ligands. Some of the effects that have been suggested include analgesia, tolerance and dependence, appetite, renal function, gastrointestinal motility, gastric secretion, learning and memory, mental illness, epileptic seizures and other neurological disorders, cardiovascular responses, and respiratory depression (see G. T. Shearman et al. *J. Pharmacol. Exp. Ther.*, 243, 591-597, 1987).

The fact that the effects of endogenous and exogenous opioids are mediated by at least three different types of opioid receptors raises the possibility that highly selective exogenous opioid agonist or antagonist ligands might have therapeutic applications. Thus, if a ligand acts at a single opioid receptor type or subtype, the potential side effects mediated through other opioid receptor types can be minimized or eliminated.

The selectivities of the prototypical delta (naltrindole, U.S. Pat. No. 4,816,586) and kappa (norbinaltorphimine, nor-BNI, U.S. Pat. No. 4,649,200) opioid antagonists have been attributed to the presence of non-peptide "address mimics" which bear a functional relationship to key motifs in the putative delta and kappa addresses of the endogenous opioid peptides, dynorphin-A and enkephalin, respectively. P. S. Portoghese et al. *J. Med. Chem.* 1993, 36, 179-180 and U.S. Pat. No. 5,457,208 reported a series of NTI analogues in which the C5' position of the indolic benzenoid ring is substituted with an alkyl amidine pendant.

U.S. Pat. No. 6,500,824 discusses a series of compounds that are reported to have activity as kappa antagonists and to be useful for treating conditions wherein antagonism of kappa receptors is indicated. One specific compound prepared therein is the compound 5'-guanidinyl-17-cyclopropylmethyl-6,7-didehydro-4,5-α-epoxy-3,14-dihydroxyindolo[2',3':6,7]-morphinan ditrifluoroacetate dehydrate (Example 1 therein):

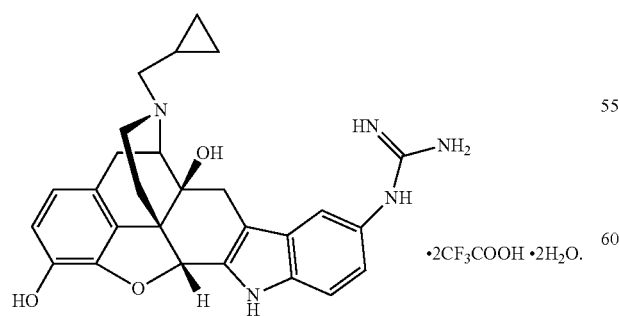

·2CF₃COOH ·2H₂O.

Currently, the corresponding bis-hydrochloride salt (GNTI bis-hydrochloride) is under development for the treatment of type-2 diabetes. In spite of this, there is currently a need for compounds and compositions that are more efficacious and/or that have greater stability than the GNTI bis-hydrochloride salt.

Lipoic acid (LA) has been reported to lower glucose in experimental animals. Additionally, there is limited clinical data showing that LA can improve glucose utilization in individuals with type 2 diabetes. A clinical trial in 13 patients with type 2 diabetes found that a single intravenous infusion of LA improved insulin-stimulated glucose disposal by 50% compared to a placebo infusion (Jacob S, Henriksen et al., *Arzneimittelforschung*, 1995, 45(8), 872-874). In an uncontrolled pilot study of 20 patients with type 2 diabetes, intravenous infusion of LA for ten days also improved insulin sensitivity when measured 24 hours after the last infusion (Jacob S, Henriksen et al., *Exp Clin Endocrinol Diabetes*, 1996, 104(3), 284-288). A placebo-controlled study of 72 patients with type 2 diabetes found that oral administration of LA improved insulin sensitivity by 25% after four weeks of treatment (Jacob S, Rett et al., *Biofactors*, 1999, 10(2-3), 169-174; and Ziegler D. *Treat Endocrinol*, 2004, 3(3), 173-189).

SUMMARY

A composition has been identified that comprises the compound GNTI and lipoic acid; this composition is efficacious in the treatment of diabetes.

Accordingly, in one embodiment the invention provides a composition comprising a compound of formula (I):

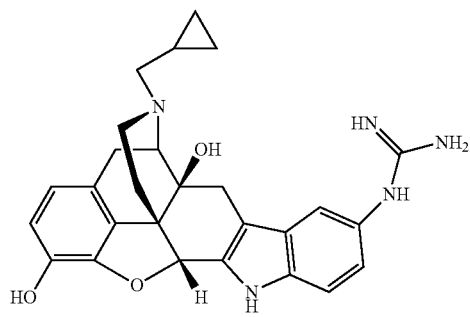

and lipoic acid.

The invention also provides a composition prepared by combining lipoic acid and a compound of formula (I):

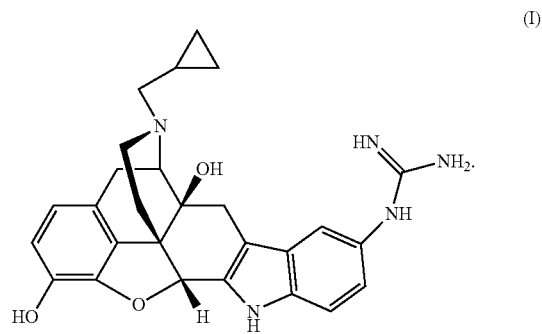

(I)

The invention also provides a lipoic acid salt of a compound of formula (I):

(I)

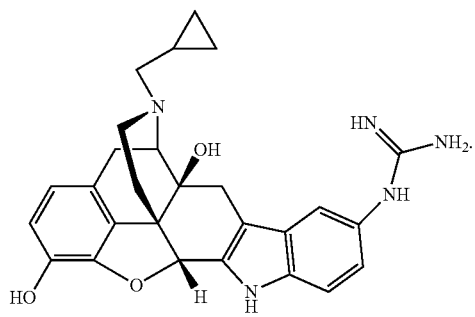

The invention also provides a salt of formula (II):

(II)

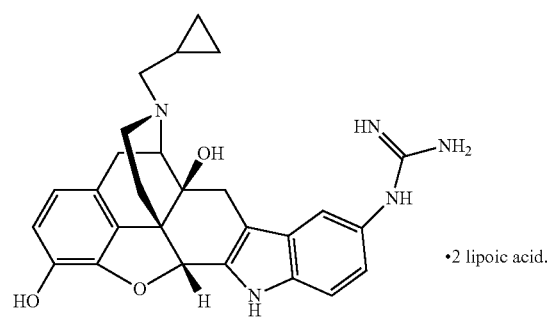

·2 lipoic acid.

The invention also provides a pharmaceutical composition comprising a pharmaceutically acceptable diluent or carrier and a salt of formula (II):

(II)

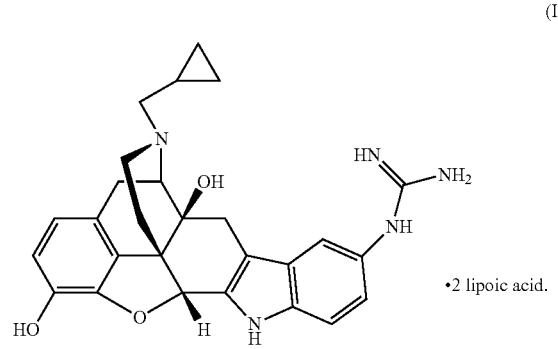

·2 lipoic acid.

Additionally, the invention provides a therapeutic method for preventing or treating a pathological condition or symptom in a mammal, such as a human, wherein kappa receptor activity is implicated and antagonism of kappa receptors is desired comprising administering to the mammal, an effective amount of a salt of the invention or a composition of the invention.

The invention provides a salt of the invention or a composition of the invention for use in medical therapy (preferably for use in treating conditions wherein antagonism of kappa receptors is indicated, e.g. for appetite suppression, as an antipsychotic, or to treat paralysis due to ischemic spinal cord injury), as well as the use of salt of the invention or a composition of the invention for the manufacture of a medicament for the treatment of a pathological condition or symptom in a mammal, such as a human, wherein antagonism of kappa receptors is indicated.

Additionally, the invention provides a therapeutic method for preventing or treating disease, including but not limited to diabetes (e.g. type-2 diabetes) in a mammal, such as a human, comprising administering to the mammal, an effective amount of a salt of the invention or a composition of the invention.

The invention provides a salt of the invention or a composition of the invention for the therapeutic or prophylactic treatment of disease (e.g. type-2 diabetes), as well as the use of salt of the invention or a composition of the invention for the manufacture of a medicament for the treatment of disease (e.g. type-2 diabetes) in a mammal, such as a human.

The invention also provides novel processes and intermediates described herein that are useful for preparing a composition or a salt of the invention.

The salt and the compositions of the invention have advantages over GNTI bis-hydrochloride for treating type-2 diabetes, including the presence of lipoic acid, which has activity as a modulator of insulin sensitivity in patients with type-2 diabetes.

DETAILED DESCRIPTION

Figure 1:
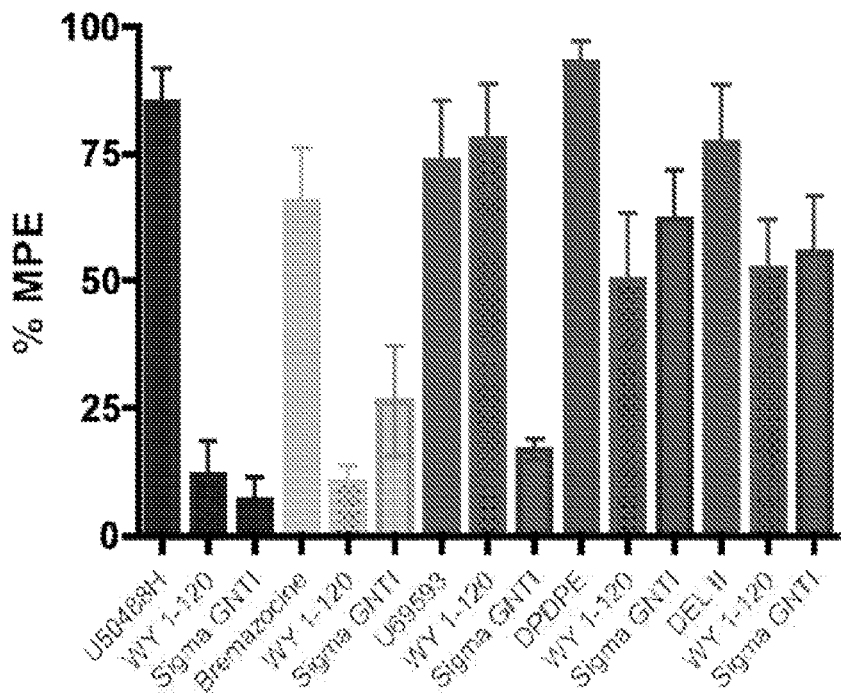
FIG. 1 Shows a comparison of data for GNTI.2HCl and GNTI.2LA in a Tail Flick Assay when administered I.T.

All references to the Periodic Table of the Elements refer to the Periodic Table of the Elements published and copyrighted by CRC Press, Inc., 1990. Also, any references to a Group or Groups shall be to the Group or Groups reflected in this Periodic Table of the Elements using the IUPAC system for numbering groups. Unless stated to the contrary, implicit from the context, or customary in the art, all parts and percent are based on weight and all test methods are current as of the filing date of this disclosure. For purposes of United States patent practice, the contents of any referenced patent, patent application or publication are incorporated by reference in their entirety (or its equivalent US version is so incorporated by reference) especially with respect to the disclosure of synthetic techniques, product and processing designs, polymers, catalysts, definitions (to the extent not inconsistent with any definitions specifically provided in this disclosure), and general knowledge in the art.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, viscosity, melt index, etc., is from 100 to 1,000, the intent is that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, the weight percent of components within compositions disclosed herein.

The term "about," as used herein in conjunction with a numerical range, modifies that range by extending the boundaries above and below the numerical values set forth. In one embodiment, the term "about" is used herein to modify a numerical value above and below the stated value by a variance of 10%. Therefore, about 50% includes the range of 45%-55%.

The term "administering" refers to bringing a subject in contact with compositions and salts of the invention. Administration can be accomplished in vitro, i.e. in a test tube, or in vivo, i.e. in cells or tissues of living organisms, for example humans. In one embodiment, the invention encompasses administering the compositions and salts of the invention to a subject.

As used with respect to a chemical compound, unless specifically indicated otherwise, the singular includes all isomeric forms and vice versa (for example, "hexane", includes all isomers of hexane individually or collectively). The terms "compound" and "complex" are used interchangeably to refer to organic-, inorganic- and organometal compounds. The term, "atom" refers to the smallest constituent of an element regardless of ionic state, that is, whether or not the same bears a charge or partial charge or is bonded to another atom.

"Comprising," "including," "having" and like terms are not intended to exclude the presence of any additional component, step or procedure, whether or not the same is specifically disclosed. In order to avoid any doubt, all processes claimed through use of the term "comprising" may include one or more additional steps, pieces of equipment or component parts, and/or materials unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed. The term "or," unless stated otherwise, refers to the listed members individually as well as in any combination.

The term "composition" refers to a mixture or blend of two or more components.

The term "diabetes" refers to high blood sugar or ketoacidosis, as well as chronic, general metabolic abnormalities arising from a prolonged high blood sugar status or a decrease in glucose tolerance. "Diabetes" encompasses both the type I and type II (Non-Insulin Dependent Diabetes Mellitus or NIDDM) forms of the disease. The risk factors for diabetes include the following factors: waistline of more than 40 inches for men or 35 inches for women, blood pressure of 130/85 mmHg or higher, triglycerides above 150 mg/dl, fasting blood glucose greater than 100 mg/dl or high-density lipoprotein of less than 40 mg/dl in men or 50 mg/dl in women.

The term "late stage type 2 diabetes mellitus" includes patients with a secondary drug failure, indication for insulin therapy and progression to micro- and macrovascular complications e.g. diabetic nephropathy, coronary heart disease (CHD).

The term "effective" amount or a "therapeutically effective amount" of a composition refers to a nontoxic but sufficient amount of the composition or salt to provide the desired effect.

The term "hyperinsulinemia" refers to a state in an individual in which the level of insulin in the blood is higher than normal.

The term "insulin resistance" refers to a state in which a normal amount of insulin produces a subnormal biologic response relative to the biological response in a subject that does not have insulin resistance.

An "insulin resistance disorder" refers to any disease or condition that is caused by or contributed to by insulin resistance. Examples include: diabetes, obesity, metabolic syndrome, insulin-resistance syndromes, syndrome X, insulin resistance, high blood pressure, hypertension, high blood cholesterol, dyslipidemia, hyperlipidemia, dyslipidemia, atherosclerotic disease including stroke, coronary artery disease or myocardial infarction, hyperglycemia, hyperinsulinemia and/or hyperproinsulinemia, impaired glucose tolerance, delayed insulin release, diabetic complications, including coronary heart disease, angina pectoris, congestive heart failure, stroke, cognitive functions in dementia, retinopathy, peripheral neuropathy, nephropathy, glomerulonephritis, glomerulosclerosis, nephrotic syndrome, hypertensive nephrosclerosis some types of cancer (such as endometrial, breast, prostate, and colon), complications of pregnancy, poor female reproductive health (such as menstrual irregularities, infertility, irregular ovulation, polycystic ovarian syndrome (PCOS)), lipodystrophy, cholesterol related disorders, such as gallstones, cholescystitis and cholelithiasis, gout, obstructive sleep apnea and respiratory problems, osteoarthritis, and prevention and treatment of bone loss, e.g. osteoporosis.

The term "metabolic syndrome" may include, but is not limited to, atherogenic dyslipidemia, pre-diabetes, overweight/obesity, Type 2 diabetes mellitus and essential hypertension. The pathogenesis of obesity is associated with other components of the metabolic syndrome, e.g., atherogenic dyslipidemia, and glucose intolerance, the magnitude of which may progress, from its initial stages characterized by impaired fasting glucose, followed by impaired glucose tolerance and culminating in Type 2 diabetes mellitus.

The term "patient," "individual," "subject" or "host" refers to either a human or a non-human animal.

The term "pre-diabetes" is the condition wherein an individual is pre-disposed to the development of type 2 diabetes. Pre-diabetes extends the definition of impaired glucose tolerance to include individuals with a fasting blood glucose within the high normal range 100 mg/dL (J. B. Meigs, et al. *Diabetes* 2003; 52:1475-1484) and fasting hyperinsulinemia (elevated plasma insulin concentration). The scientific and medical basis for identifying pre-diabetes as a serious health threat is laid out in a Position Statement entitled "The Prevention or Delay of Type 2 Diabetes" issued jointly by the American Diabetes Association and the National Institute of Diabetes and Digestive and Kidney Diseases (Diabetes Care 2002; 25:742-749).

The term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

In one embodiment, the term "predisposed to" is to be considered to refer to, inter alia, a genetic profile or familial relationship which is associated with a trend or statistical increase in incidence, severity, etc. of the indicated disease. In one embodiment, the term "predisposed to" refers to, inter alia, a lifestyle that is associated with increased risk of the indicated disease. In some embodiments, the term "predisposed to" is to be considered to refer to inter alia, the presence of biomarkers which are associated with the indicated disease, for example, in cancer, the term "predisposed to" the cancer may comprise the presence of precancerous precursors for the indicated cancer.

The term "progression" refers to an increasing in scope or severity, advancing, growing or becoming worse.

The term "recurrence" refers to a return of a disease after a remission.

In some embodiments, the term "reducing the pathogenesis" is to be understood to encompass reducing tissue damage, or organ damage associated with a particular disease, disorder or condition. In another embodiment, the term "reducing the pathogenesis" is to be understood to encompass reducing the incidence or severity of an associated disease, disorder or condition, with that in question. In another embodiment, the term "reducing the pathogenesis" is to be understood to encompass reducing the number of associated diseases, disorders or conditions with the indicated, or symptoms associated thereto.

The term "treatment" refers to delayed progression of, prolonged remission of, reduced incidence of, or amelioration of symptoms associated with the disease, disorder or condition.

The term "treating" and its included aspects, refers to the administration to a subject with the indicated disease, disorder or condition, or in some embodiments, to a subject predisposed to the indicated disease, disorder or condition.

The terms "treating" or "treatment" includes preventative as well as disorder remitative treatment.

The terms "reducing," "suppressing," and "inhibiting" have their commonly understood meaning of lessening, decreasing, or delaying the incidence, severity or pathogenesis of a disease, disorder or condition. In another embodiment, the terms "treating," "reducing," "suppressing" or "inhibiting" refer to a reduction in morbidity, mortality, or a combination thereof, in association with the indicated disease, disorder or condition.

The term "weight management" means controlling body weight and in the context of the present disclosure is directed toward weight loss and the maintenance of weight loss (also called weight maintenance herein). In addition to controlling body weight, weight management includes controlling parameters related to body weight, for example, BMI, percent body fat and waist circumference. For example, weight management for an individual who is overweight or obese can mean losing weight with the goal of keeping weight in a healthier range. Also, for example, weight management for an individual who is overweight or obese can include losing body fat or circumference around the waist with or without the loss of body weight. Maintenance of weight loss (weight maintenance) includes preventing, reducing or controlling weight gain after weight loss. It is well known that weight gain often occurs after weight loss. Weight loss can occur, for example, from dieting, exercising, illness, drug treatment, surgery or any combination of these methods, but often an individual that has lost weight will regain some or all of the lost weight. Therefore, weight maintenance in an individual who has lost weight can include preventing weight gain after weight loss, reducing the amount of weigh gained after weight loss, controlling weight gain after weight loss or slowing the rate of weight gain after weight loss.

Then term "weight management in an individual in need thereof" refers to a judgment made by a healthcare practitioner that an individual requires or will benefit from weight management treatment. This judgment is made based on a variety of factors that are in the realm of a healthcare practitioner's expertise, but that includes the knowledge that the individual has a condition that is treatable by the methods disclosed herein.

U.S. Pat. No. 6,500,824 discusses a series of compounds that are reported to have activity as kappa antagonists and to be useful for treating conditions wherein antagonism of kappa receptors is indicated. One specific compound prepared therein is the compound 5'-guanidinyl-17-cyclopropylmethyl-6,7-didehydro-4,5-α-epoxy-3,14-dihydroxyindolo[2',3':6,7]-morphinan ditrifluoroacetate dehydrate (Example 1 therein):

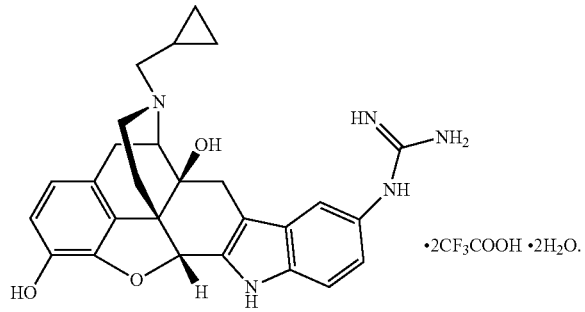

Alpha-lipoic acid, commonly known as lipoic acid, has a variety of names, including thioctic acid, 1,2-dithiolane-3-pentanoic acid, 1,2-ditholane-3-valeric acid, 6,8-thioctic acid5-[3C1,2-dithiolanyl)]-pentanoic acid, delta-[3-(1, 2dithiacyclopentyl)]pentanoic acid and pyruvate oxidation factor. Alpha lipoic acid has an asymmetric center and is usually employed in the form of a racemic mixture of its R- and S-enantiomers, particularly in nutritional supplements.

Alpha-lipoic acid (herein referred to as lipoic acid) is an antioxidant and is a scavenger of reactive oxygen species (ROS). It chelates metals and recycles endogenous antioxidants. Lipoic acid can scavenge singlet oxygen, $H_2O_2$, hydroxyl radical, NO, and ONOO—. The reduced form of lipoic acid, dihydrolipoic acid, can further scavenge $O_2.^-$, and peroxy radicals. Lipoic acid can also chelate several divalent cations, e.g., $Mn^{2+}$, $Cu^{2+}$, $Zn^{2+}$, $Cd^{2+}$, and $Pb^{2+}$.

Therefore, lipoic acid can inhibit ascorbate-induced production of $H_2O_2$ by $Cu^{2+}$. Lipoic acid can recycle endogenous antioxidants, such as glutathione (GSH), and vitamin C. GSH protects tissues from oxidative stress. Lipoic acid can also circulate plasma levels of lactate and pyruvate in diabetic patients. Estrada et al., (*Diabetes.* 1996, 45, 1798-1804) report that lipoic acid induces GLUTs (glucose transporters) and glucose uptake and this suggests that lipoic acid may also stimulate the insulin signaling pathway.

Lipoic acid administration has been shown to be active in oxidative stress models including in ischemia-reperfusion injury model. Furthermore, lipoic acid can function as a redox regulator of thioredoxin and NF-☐ B transcription factor.

The salts of the invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

The present compositions and salts may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compositions and salts may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the compositions and salts may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compositions and salts can be determined by comparing their in vitro activity, and in vivo activity in animal models. Methods for the extrapolation of effective dosages in mice, and other animals, to humans are known to the art; for example, see U.S. Pat. No. 4,938,949.

The amount of the composition or salt required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The ability of a composition or salt of the invention to treat type-2 diabetes can be determined using pharmacological models which are well known to the art. For example, the ability of a composition or salt of the invention to treat type-2 diabetes can be determined using the animal model of type 2 diabetes described by D. Feliers, et al, *Kidney*

*International* (2001) 60, 495-504, in which the db/db mouse strain is used as a model of type 2 diabetes, and its lean littermate as the control (Jackson Labs, Bar Harbor Me., USA). Their phenotype consists of obesity, insulin resistance, and diabetes, similar to type 2 diabetes in humans. The renal functional and histologic abnormalities have been described in the db/db mice. The db/db mice develop progressive renal histologic changes and functional derangements, including loss of renal function, similar to humans with type 2 diabetes.

In one embodiment, the methods of treatment of the invention reduce the severity of the disease, or in another embodiment, symptoms associated with the disease.

In one embodiment, this invention provides a method of treating, suppressing, inhibiting, reducing the severity of, reducing the incidence of, reducing pathogenesis of or delaying onset of an insulin resistance disorder.

In one embodiment, this invention provides a method of treating, suppressing, inhibiting, reducing the severity of, reducing the incidence of, reducing pathogenesis of or delaying onset of disease including but not limited to (a) diabetes; (b) glucose intolerance; (c) hyperinsulinemia; (d) insulin resistance; (e) diabetic nephropathy; (f) diabetic neuropathy; (g) fatty liver conditions, (h) cardiovascular disease; (i) cachexia in a human subject; (j) atherogenic dyslipidemia; (k) weight management; and (l) impaired glucose tolerance, comprising the step of administering to the subject compositions and salts of the invention.

In yet another embodiment, this invention provides a method of treating, suppressing, inhibiting, reducing the severity of, reducing the incidence of, reducing pathogenesis of or delaying onset of diabetes including but not limited to pre-diabetes, incipient diabetes, type-1 diabetes, and type-2 diabetes.

The administration of a composition or salt of the invention to a subject in need thereof may treat metabolic syndrome. Administration of a composition or salt of the invention may treat metabolic syndrome by restoring the incretin effect, by restoring physiologic control of glucagon levels, by restoring the physiologic glucose dependent insulin secretion, and/or by restoring first-phase insulin secretion.

In another embodiment, the administration of a composition or salt of the invention may also treat overweight, atherogenic dyslipidemia obesity or type-2 diabetes mellitus by restoring the incretin effect, by restoring physiologic control of glucagon levels, by restoring the physiologic glucose dependent insulin secretion, and/or by restoring first-phase insulin secretion.

In yet another embodiment, the administration of a composition or salt of the invention to a subject in need thereof restores the incretin effect. In a subject having a normal response to oral nutrient administration, the release of the insulinotropic hormones, GIP and GLP-1, results in an increase in insulin secretion. This is called the "incretin effect."

As used herein, to "restore," for example, with respect to the incretin effect, suitably includes enhancing, potentiating, increasing, reestablishing, re-activating, or improving the physiological state. For example, a subject having type-2 diabetes mellitus may exhibit diminished or even zero incretin effect, i.e., diminished or no activity of GIP or GLP-1, or diminished or no increase in insulin secretion upon nutrient administration. Consequently, to "restore" the incretin effect suitably increases, though does not necessarily normalize, GIP or GLP-1 activity or insulin secretion upon nutrient administration in a subject.

In another embodiment, the administration of a composition or salt of the invention may restore physiologic control of glucagon levels in a subject in need thereof. As used herein, to "restore," for example with respect to physiologic control of glucagon levels, suitably includes decreasing, lowering, regulating, reestablishing, or improving the physiologic state.

In a subject having a 'normal' physiologic response to nutrient administration, physiologic control of glucagon primarily responds to blood glucose levels, i.e., as blood glucose levels decline, glucagon is released from the α-cells of the islets of Langerhans in the pancreas, and act on the liver to induce gluconeogenesis, i.e., endogenous glucose production, and/or glycogenolysis. Conversely, glucagon release decreases in response to increasing blood glucose levels. Additionally, glucagon levels decrease in response to release of insulin by pancreatic β-cells. Consequently, in a subject having abnormal insulin production or release in response to increasing blood glucose levels, glucagon release may remain abnormally high and result in hyperglucagonemia, which further exacerbates conditions such as type-2 diabetes mellitus and impaired glucose tolerance.

In one embodiment, administration of a composition or salt of the invention restores first-phase insulin secretion in a subject in need thereof. The administration of a composition or salt of the invention may restore the physiologic glucose dependent insulin secretion in a subject in need thereof, and a composition or salt of the invention may restore the physiologic control of glucagon release.

Normal insulin secretion from the pancreatic 13 cells is biphasic. The initial release of insulin that acts on the pancreatic α-cells to decrease glucagon is referred to as the first-phase of insulin secretion. First-phase insulin secretion is characterized by a rapid and sizable increase in insulin, beginning within two minutes of nutrient ingestion, and continuing for 10-15 minutes. The second phase of insulin secretion follows and insulin secretion peaks approximately 1-2 hours following nutrient ingestion. Insulin secretion continues until normal blood glucose levels are restored. Often, in subjects having impaired glucose tolerance, first-phase insulin secretion is reduced and it is believed that the reduction in first-phase insulin secretion may be a preliminary sign in the progression of type-2 diabetes mellitus.

The dosage of compositions disclosed herein will vary widely, depending upon the frequency of administration, the manner of administration, and the clearance of the composition from the subject. It will be appreciated that the specific dosage administered in any given case will be adjusted in accordance with the condition of the subject and other relevant medical factors that may modify the activity of the administered compositions.

For example, the specific dose for a particular patient depends on age, body weight, general state of health, diet, the timing and mode of administration, the rate of excretion and medicaments used in combination. For example, a suitable weekly dose of a composition disclosed herein may be less than about 300 ng per kg of body weight. Alternatively the weekly dose of a composition disclosed herein may be less than about 200 ng per kg of body weight, less than about 150 ng per kg of body weight or less than about 100 ng per kg of body weight. The initial dose may be larger, followed by smaller maintenance doses. The dose may be administered as infrequently as weekly or biweekly, or fractionated into smaller doses and administered daily, semi-weekly, etc. to maintain an effective dosage level. A suitable daily dosage of a composition disclosed herein is less than about 80 ng per kg of body weight. Alternatively the daily dosage of a composition disclosed herein may be less than about 50 ng per kg of body weight, less than about 25 ng per kg of body weight, or less than about 20 ng per kg of body weight.

In some embodiments, administration of one or more compositions disclosed herein provides an improvement in one or more cardiovascular indications. In some embodiments, the improvement in one or more cardiovascular indications comprises one or more of a reduction in systolic and diastolic blood pressure (SBP and DBP, respectively), a decrease in heart rate, a decrease in total cholesterol, a decrease in LDL cholesterol, a decrease in HDL cholesterol, and/or a decrease in triglyceride levels.

In some embodiments, the one or more additional beneficial effects comprise a reduction in SBP.

In some embodiments, the reduction in SBP in an individual is at least about 2 mmHg. In some embodiments, the reduction in SBP in an individual is between 2 and 5 mmHg. In some embodiments, the reduction in SBP in an individual is about 3 mmHg. In some embodiments, the reduction in SBP in an individual is about 3.5 mmHg.

In some embodiments, the one or more additional beneficial effects comprise a reduction in DBP.

In some embodiments, the reduction in DBP in an individual is at least about 1 mmHg. In some embodiments, the reduction in DBP in an individual is at least between about 1 and 5 mmHg. In some embodiments, the reduction in DBP in an individual is about 2 mmHg. In some embodiments, the reduction in DBP in an individual is about 2.5 mmHg. In some embodiments, the reduction in DBP in an individual is about 3 mmHg.

In some embodiments, the one or more additional beneficial effects comprise a reduction in heart rate.

In some embodiments, the reduction in heart rate in an individual is at least about 2 beats per minute (BPM). In some embodiments, the reduction in heart rate in an individual is between about 2 and 5 BPM. In some embodiments, the reduction in heart rate in an individual is about 2 BPM. In some embodiments, the reduction in heart rate in an individual is about 2.5 BPM. In some embodiments, the reduction in heart rate in an individual is about 3 BPM. In some embodiments, the reduction in heart rate in an individual is about 3.5 BPM. In some embodiments, the reduction in heart rate in an individual is about 4 BPM.

In some embodiments, the improvement in glycemia comprises a decrease in total cholesterol level.

In some embodiments, the decrease in total cholesterol level is at least about 0.5 mg/dL. In some embodiments, the decrease in total cholesterol level is between about 0.5 and 1 mg/dL. In some embodiments, the decrease in total cholesterol level is about 0.7 mg/dL.

In other embodiments, the decrease in total cholesterol level is at least about 1 mg/dL. In some embodiments, the decrease in total cholesterol level is at least about 1.5 mg/dL. In some embodiments, the decrease in total cholesterol level is between about 1.5 and 2 mg/dL. In some embodiments, the decrease in total cholesterol level is about 1.7 mg/dL.

In other embodiments, the decrease in total cholesterol level is at least about 2 mg/dL. In some embodiments, the decrease in total cholesterol level is between about 2 and 3 mg/dL. In some embodiments, the decrease in total cholesterol level is about 2.3 mg/dL.

In some embodiments, the improvement in glycemia comprises a decrease in LDL cholesterol level.

In some embodiments, the decrease in LDL cholesterol level is at least about 1 mg/dL. In some embodiments, the decrease in LDL cholesterol level is between about 1 and 1.5 mg/dL. In some embodiments, the decrease in LDL cholesterol level is between about 1 and 2 mg/dL. In some embodiments, the decrease in LDL cholesterol level is at least about 2 mg/dL. In some embodiments, the decrease in LDL cholesterol level is between about 2 and 3 mg/dL. In some embodiments, the decrease in LDL cholesterol level is about 2.5 mg/dL.

In some embodiments, the improvement in glycemia comprises a decrease in HDL cholesterol level.

In some embodiments, the decrease in HDL cholesterol level is at least about 2 mg/dL. In some embodiments, the decrease in HDL cholesterol level is between about 2 and 3 mg/dL. In some embodiments, the decrease in HDL cholesterol level is at least about 4 mg/dL. In some embodiments, the decrease in HDL cholesterol level is between about 3 and 6 mg/dL.

In some embodiments, the decrease in HDL cholesterol level is at least about 5 mg/dL. In some embodiments, the decrease in HDL cholesterol level is at least about 7 mg/dL. In some embodiments, the decrease in HDL cholesterol level is between about 7 and 10 mg/dL.

In some embodiments, the one or more additional beneficial effects comprise an improvement in glycemia. In some embodiments, the improvement in glycemia comprises a reduction in fasting plasma glucose and/or a reduction in glycated hemoglobin (A1C) levels.

In some embodiments, the improvement in glycemia comprises a reduction in fasting plasma glucose.

In some embodiments, the reduction in fasting plasma glucose is at least about 1 mg/dL. In some embodiments, the reduction in fasting plasma glucose is at least about 1.5 mg/dL. In some embodiments, the reduction in fasting plasma glucose is between about 1 and 4 mg/dL. In some embodiments, the reduction in fasting plasma glucose is at least about 5 mg/dL. In some embodiments, the reduction in fasting plasma is between about 5 and 10 mg/dL In some embodiments, the reduction in fasting plasma glucose is at least about 10 mg/dL. In some embodiments, the reduction in fasting plasma glucose is between about 10 and 40 mg/dL. In some embodiments, the reduction in fasting plasma glucose is about 25 mg/dL. In some embodiments, the reduction in fasting plasma glucose is about 30 mg/dL.

In some embodiments, the improvement in glycemia comprises a reduction in glycated hemoglobin (A1C) levels.

In some embodiments, the reduction in glycated hemoglobin (A1C) level is between about 0.05 and 0.2%. In some embodiments, the reduction in glycated hemoglobin (A1C) level is at least about 0.1%. In some embodiments, the reduction in glycated hemoglobin (A1C) level is between about 0.1 and 0.2%. In some embodiments, the reduction in glycated hemoglobin (A1C) level is about 0.15%. In some embodiments, the reduction in glycated hemoglobin (A1C) level is about 0.18%. In some embodiments, the reduction in glycated hemoglobin (A1C) level is at least about 0.5%. In some embodiments, the reduction in glycated hemoglobin (A1C) level is between about 1 and 2%. In some embodiments, the reduction in glycated hemoglobin (A1C) level is at least about 0.05%.

In some embodiments, the improvement in glycemia comprises a decrease in triglyceride levels.

In some embodiments, the decrease in triglyceride level is at least about 5 mg/dL. In some embodiments, the decrease in triglyceride level is between about 5 and 20 mg/dL. In some embodiments, the decrease in triglyceride level is about 14 mg/dL. In some embodiments, the decrease in triglyceride level is at least about 10 mg/dL. In some embodiments, the decrease in triglyceride level is between about 10 and 20 mg/dL.

In some embodiments, methods provided herein may further include administering at least one other agent in addition to the compositions disclosed herein.

Contemplated other agents include those administered to treat type 2 diabetes such as sulfonylureas (e.g., chlorpropamide, glipizide, glyburide, glimepiride); meglitinides (e.g., repaglinide and nateglinide); biguanides (e.g., metformin); thiazolidinediones (rosiglitazone, troglitazone, and pioglitazone); glucagon-like 1 peptide mimetics (e.g. exenatide and liraglutide); sodium-glucose cotransporter inhibitors (e.g., dapagliflozin), renin inhibitors, and alpha-glucosidase inhibitors (e.g., acarbose and meglitol), and/or those administered to treat cardiac disorders and conditions, such hypertension, dyslipidemia, ischemic heart disease, cardiomyopathy, cardiac infarction, stroke, venous thromboembolic disease and pulmonary hypertension, which have been linked to overweight or obesity, for example, chlorthalidone; hydrochlorothiazide; indapamide, metolazone; loop diuretics (e.g., bumetanide, ethacrynic acid, furosemide, lasix, torsemide); potassium-sparing agents (e.g., amiloride hydrochloride, spironolactone, and triamterene); peripheral agents (e.g., reserpine); central alpha-agonists (e.g., clonidine hydrochloride, guanabenz acetate, guanfacine hydrochloride, and methyldopa); alpha-blockers (e.g., doxazosin mesylate, prazosin hydrochloride, and terazosin hydrochloride); beta-blockers (e.g., acebutolol, atenolol, betaxolol, nisoprolol fumarate, carteolol hydrochloride, metoprolol tartrate, metoprolol succinate, Nadolol, penbutolol sulfate, pindolol, propranolol hydrochloride, and timolol maleate); combined alpha- and beta-blockers (e.g., carvedilol and labetalol hydrochloride); direct vasodilators (e.g., hydralazine hydrochloride and minoxidil); calcium antagonists (e.g., diltiazem hydrochloride and verapamil hydrochloride); dihydropyridines (e.g., amlodipine besylate, felodipine, isradipine, nicardipine, nifedipine, and nisoldipine); ACE inhibitors (benazepril hydrochloride, captopril, enalapril maleate, fosinopril sodium, lisinopril, moexipril, quinapril hydrochloride, ramipril, trandolapril); angiotensin II receptor blockers (e.g., losartan potassium, valsartan, and Irbesartan); and combinations thereof, as well as statins such as mevastatin, lovastatin, pravastatin, simvastatin, velostatin, dihydrocompactin, fluvastatin, atorvastatin, dalvastatin, carvastatin, carvastatin, bevastatin, cefvastatin, rosuvastatin, pitavastatin, and glenvastatin, typically for treatment of dyslipidemia.

The invention will now be illustrated by the following non-limiting Examples.

EXAMPLES

Example 1

Conversion of GNTI Free Base to GNTI Dilipoate (GNTI.2LA)

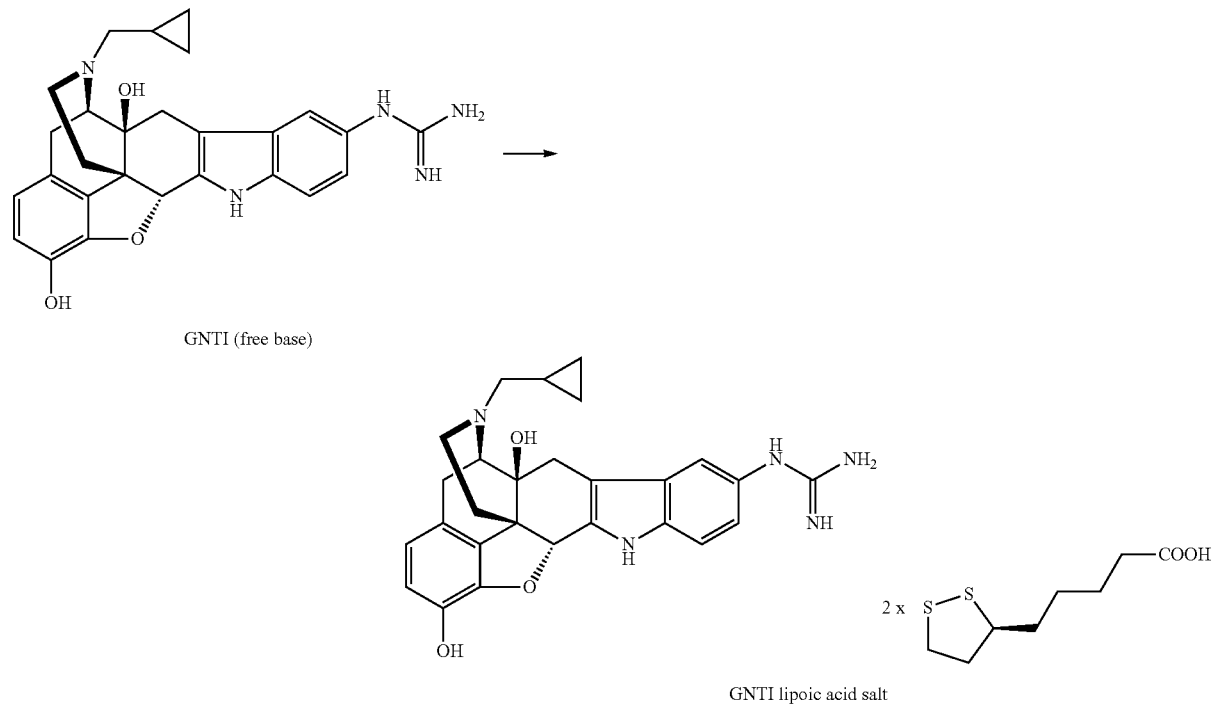

GNTI (free base)

GNTI lipoic acid salt

To a suspension of GNTI free base (100 mg, 0.21 mmol) in MeOH (50 mL) was added α-lipoic acid (87.5 mg, 0.42 mmol, 2.0 eq.) and the mixture was stirred at room temperature in the dark. The suspension turned to a clear solution upon addition of α-lipoic acid. The solvent was removed in vacuo to afford 150 mg (80%) of GNTI.2LA as tan solid having a NMR spectrum consistent with a salt containing two equivalents of lipoic acid to one equivalent of GNTI.

The intermediate GNTI free base was prepared as follows
a. Preparation of GNTI Base from GNTI2HCl

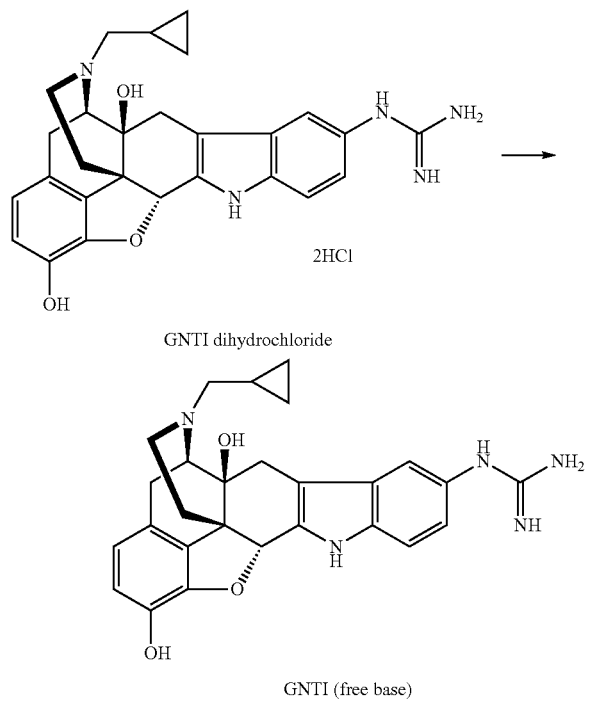

To a solution of GNTI.2HCI (1.0 g, 1.84 mmol) in CH$_2$Cl$_2$/MeOH (250 mL/70 mL) there was added 28% aq NH$_4$OH (150 mL) and the mixture was stirred at rt. The white, solid, GNTI free base that precipitated from the organic phase was collected by filtration. The aqueous phase was then extracted an additional four times with CH$_2$Cl$_2$ and the extracts were dried over Na$_2$SO$_4$. After adding the solid GNTI base to the methylene chloride extract, the solution was evaporated in vacuo to give GNTI base as a white solid (779.8 mg, 90%).

The starting GNTI.2HCl can be prepared using procedures similar to those described in U.S. Pat. No. 6,500,824.

The ability of a composition or salt of the invention to function as a selective kappa opioid receptor antagonist can be determined using pharmacological models which are well known to the art, or using the assay described in Example 2.

Example 2

The following study was undertaken in order to confirm that the kappa antagonist selectivity of GNTI.2HCl and GNTI.2LA does not significantly differ.

The testing protocol involved the tail-flick assay. For the measurement of the tail-flick latency, ICR-CD1 mice, mice were held gently in one hand with the tail positioned in the apparatus (Tail Flick Analgesia Meter, Columbus Instruments, Columbus, Ohio) for radiant heat stimulus. The tail-flick response was elicited by applying radiant heat to the dorsal side of the tail. The intensity of the heat was set so that the mouse flicks its tail within 2 to 3 seconds. The test latency was measured before treatment of the agonist control, and again after the antagonist treatment at the time of peak agonist activity.

Figure 2:
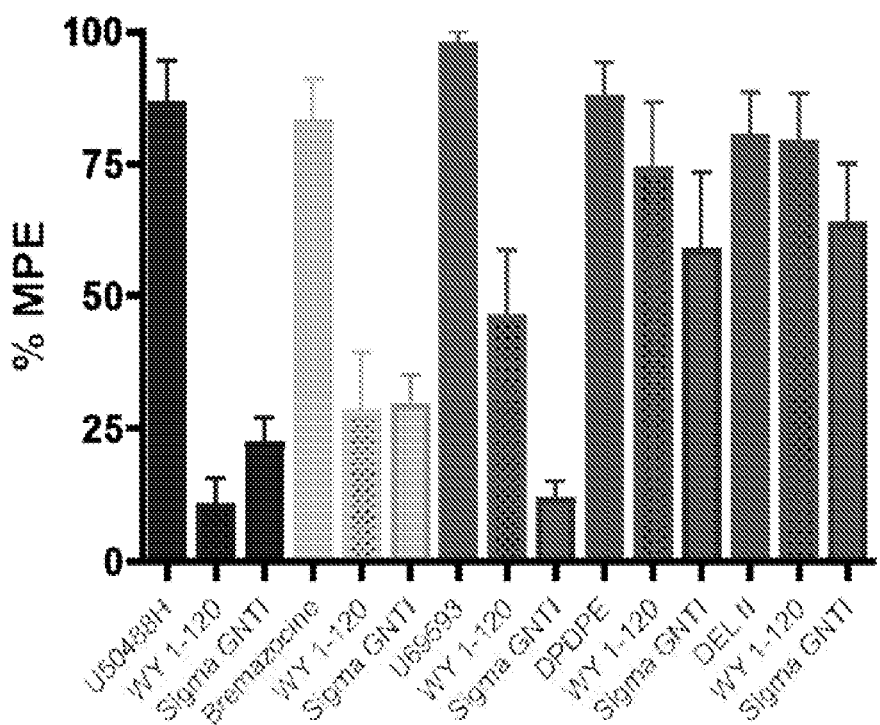
FIG. 2 Shows a comparison of data for GNTI.2HCl and GNTI.2LA in a Tail Flick Assay when administered I.C.V.

At least three groups of four to ten mice were used for each dose response curve. ED$_{50}$ values with 95% confidence intervals (C.I.) were computed with GraphPad Prism 4 using nonlinear regression methods. Ratios were considered significant if the C.I. did not overlap. Antinociception was quantified as the percent maximal possible effect (% MPE), which is calculated as: % MPE=(Test−Control/10−Control)×100. GNTI.2HCl or GNTI.2LA. The data for the dihydrochloride salt (Sigma GNTI2HCl) and the di-lipoic acid salt, GNTI.2LA (identified as WY-120) are shown in FIGS. 1 and 2. The data are expressed as bar graphs that indicate the % maximum possible effect (% MPE) of GNTI-.2HCl or GNTI.2LA in antagonizing the analgesia produced by selective kappa opioid agonists (U50488H, Bremazocine, U69593) or delta opioid agonists (DPDPE, DEL II) by the intracerebroventricular (i.c.v.) route of administration to mice.

The i.c.v. data reveal that both GNTI.2LA and GNTI.2HCI selectively antagonize the different kappa agonists, whereas the delta agonists were not significantly affected. This is consistent with the kappa opioid antagonist selectivity of GNTI.2LA, and it therefore appears that its selectivity is not significantly different from that of GNTI.2HCl. The GNTI component of both salts is therefore targeting kappa opioid receptors to the same degree.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A lipoic acid salt of a compound of formula (I):

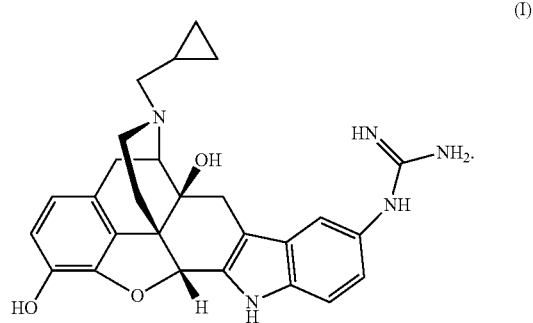

2. A salt of formula (II) or a hydrate thereof:

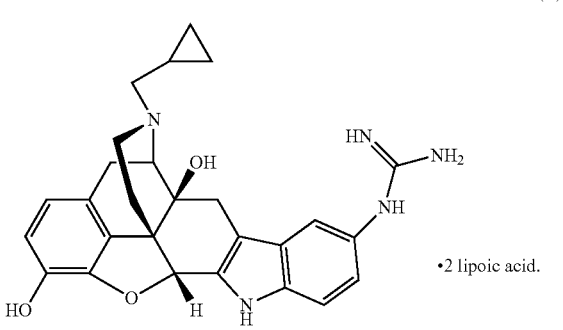

3. A composition comprising a compound of formula (I):
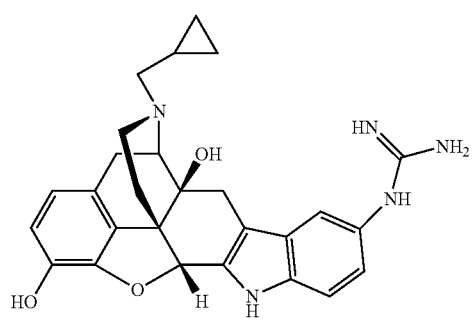
and lipoic acid.
4. A composition prepared by combining lipoic acid and a compound of formula (I):
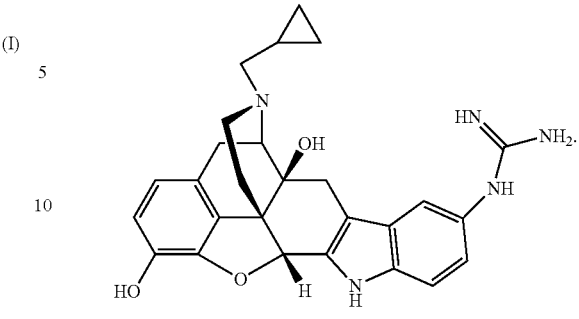
5. A pharmaceutical composition comprising a pharmaceutically acceptable diluent or carrier and a salt as described in claim 1.
* * * * *